(12) United States Patent
Mosharrafa et al.

(10) Patent No.: US 9,399,122 B2
(45) Date of Patent: *Jul. 26, 2016

(54) SYSTEMS AND METHODS FOR A TISSUE EXPANDER

(71) Applicant: Reconstructive Technologies, LLC, Phoenix, AZ (US)

(72) Inventors: Tamir M. Mosharrafa, Paradise Valley, AZ (US); Ali M. Mosharrafa, Paradise Valley, AZ (US)

(73) Assignee: Reconstructive Technologies, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/963,641

(22) Filed: Dec. 9, 2015

(65) Prior Publication Data

US 2016/0082235 A1    Mar. 24, 2016

Related U.S. Application Data

(63) Continuation-in-part of application No. 13/948,067, filed on Jul. 22, 2013.

(60) Provisional application No. 61/810,160, filed on Apr. 9, 2013, provisional application No. 62/262,837, filed on Dec. 3, 2015.

(51) Int. Cl.
*A61M 29/00* (2006.01)
*A61M 29/02* (2006.01)
(Continued)

(52) U.S. Cl.
CPC ............ *A61M 29/02* (2013.01); *A61F 2/12* (2013.01); *A61B 90/02* (2016.02); *A61F 2/52* (2013.01); *A61F 2002/523* (2013.01)

(58) Field of Classification Search
CPC ............ A61B 90/02; A61F 2/12; A61F 2/52; A61F 2002/523
See application file for complete search history.

(56) References Cited

U.S. PATENT DOCUMENTS

| | | | |
|---|---|---|---|
| 4,791,917 A | 12/1988 | Finney | |
| 4,798,205 A | 1/1989 | Bonomo et al. | |
| 4,823,815 A | 4/1989 | Watson et al. | |

(Continued)

FOREIGN PATENT DOCUMENTS

| | | | |
|---|---|---|---|
| WO | 96/40003 A1 | 12/1996 | |
| WO | 2013/012636 A2 | 1/2013 | |

*Primary Examiner* — Robert Lynch
(74) *Attorney, Agent, or Firm* — The Noblitt Group, PLLC

(57) ABSTRACT

Methods and systems for a tissue expander according to various aspects of the present invention may function in conjunction with an extended tissue expander, such as an extended tissue expander to be temporarily implanted into a patient to form a pocket for a permanent implant. Systems and methods according to various aspects of the present invention may comprise an extended tissue expander configured to increase and/or customize the size and/or shape of a tissue pocket beyond the size and/or shape provided by a conventional tissue expander. The extended tissue expander may comprise a tissue expander coupled to an extension portion. In one embodiment, the extended tissue expander may preserve a breast pocket with a desired teardrop shape that does not need extensive surgical modification before placement of a final breast implant or a tissue flap. In another embodiment, the extended tissue expander may be modified to the precise dimensions of a final breast implant for the simple exchange of the extended tissue expander for the final breast implant.

30 Claims, 16 Drawing Sheets

Figure 1A:
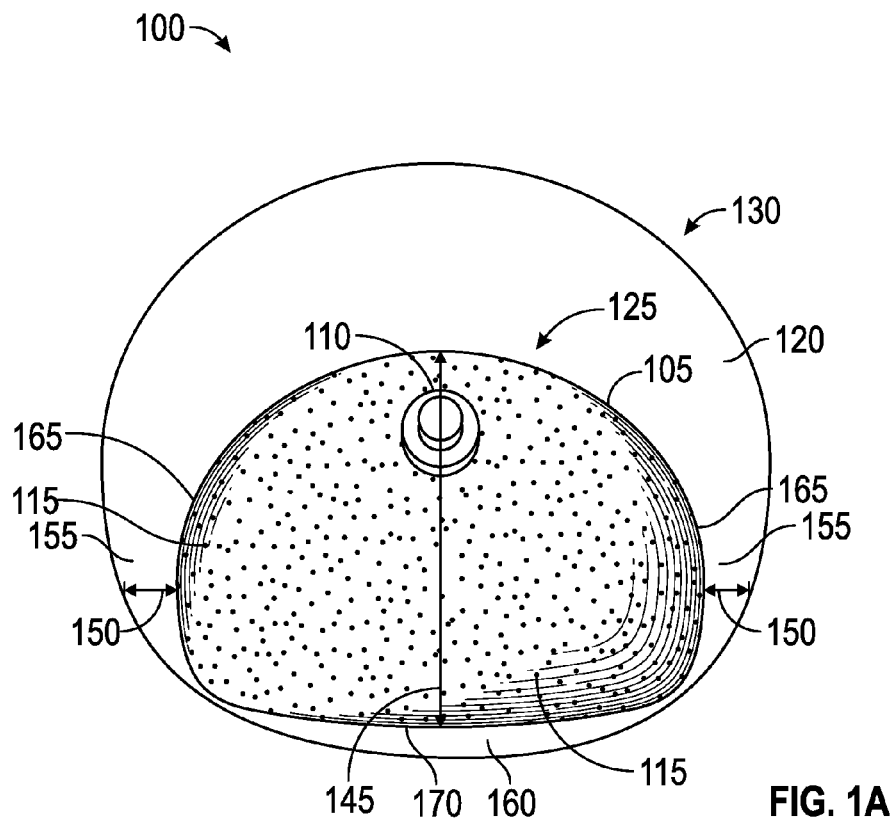

(51) Int. Cl.
  *A61F 2/12*  (2006.01)
  *A61F 2/52*  (2006.01)

(56) References Cited

U.S. PATENT DOCUMENTS

| | | | |
|---|---|---|---|
| 4,899,764 | A | 2/1990 | Gauger et al. |
| 4,902,294 | A | 2/1990 | Gosserez |
| 4,950,292 | A | 8/1990 | Audretsch |
| 4,955,395 | A | 9/1990 | Manders |
| 4,984,585 | A | 1/1991 | Austad |
| 5,033,481 | A | 7/1991 | Heyler |
| 5,049,132 | A | 9/1991 | Shaffer et al. |
| 5,066,303 | A | 11/1991 | Bark |
| 5,074,878 | A | 12/1991 | Bark et al. |
| 5,092,348 | A | 3/1992 | Maxwell et al. |
| 5,141,508 | A | 8/1992 | Bark |
| 6,228,116 | B1 | 5/2001 | Ledergerber |
| 6,315,796 | B1 | 11/2001 | Eaton |
| 6,641,527 | B2 | 11/2003 | Khouri |
| 6,666,893 | B2 | 12/2003 | Burg et al. |
| 7,238,193 | B2 | 7/2007 | Gedebou |
| 7,575,597 | B2 | 8/2009 | Rehnke |
| 8,007,532 | B2 | 8/2011 | Manders |
| 8,080,057 | B2 | 12/2011 | Kronowitz |
| 2007/0233273 | A1 | 10/2007 | Connell |
| 2010/0100114 | A1 | 4/2010 | Berger |
| 2010/0217388 | A1 | 8/2010 | Cohen et al. |
| 2011/0093070 | A1 | 4/2011 | Vardi |
| 2011/0137244 | A1 | 6/2011 | Lee et al. |
| 2012/0078366 | A1 | 3/2012 | Jones et al. |
| 2012/0123537 | A1 | 5/2012 | Manesis et al. |
| 2012/0185041 | A1 | 7/2012 | Mortarino et al. |
| 2012/0226352 | A1 | 9/2012 | Becker |
| 2012/0265165 | A1 | 10/2012 | Bucknall et al. |
| 2013/0046383 | A1 | 2/2013 | Khouri et al. |

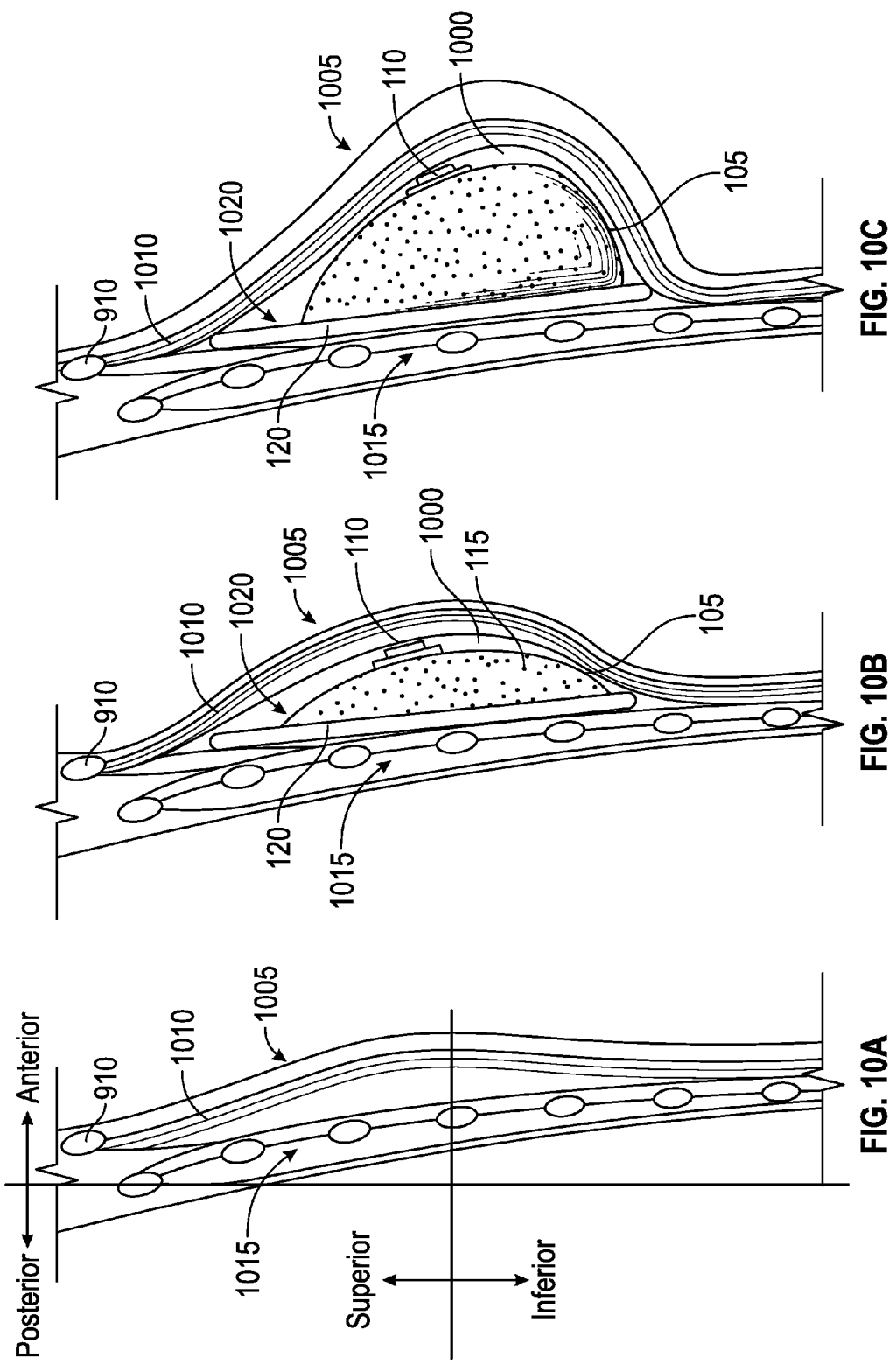

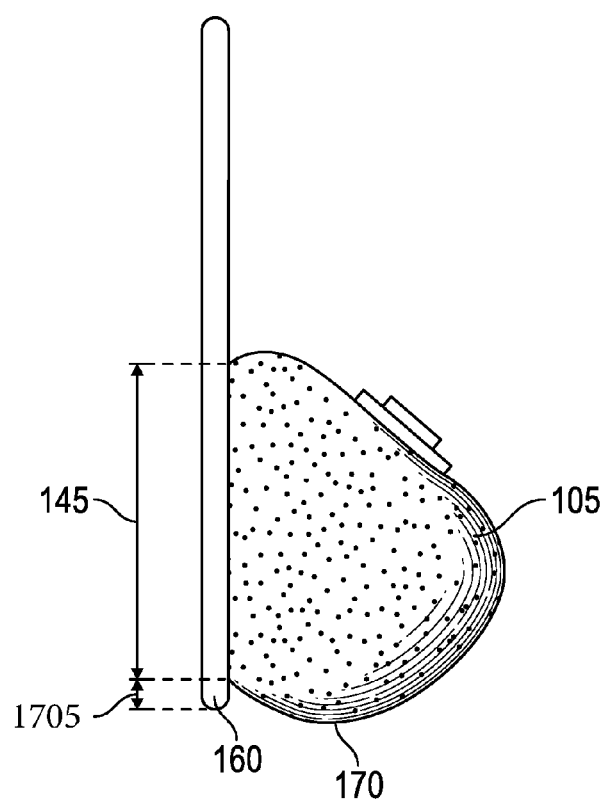
FIG. 17C

SYSTEMS AND METHODS FOR A TISSUE EXPANDER

CROSS-REFERENCE TO RELATED APPLICATIONS

This application claims the benefit of U.S. Provisional Patent Application No. 62/262,837, filed Dec. 3, 2015, and this application is a continuation-in-part of U.S. patent application Ser. No. 13/948,067, filed Jul. 22, 2013, which claims the benefit of U.S. Provisional Application No. 61/810,160, filed Apr. 9, 2013. This application incorporates the disclosure of such applications in their entirety by reference. To the extent that the present disclosure conflicts with the referenced applications, however, the present disclosure is to be given priority.

BACKGROUND

Reconstructive surgeries employ soft tissue expansion techniques to create a stretched area of skin for prosthetic implant placement. A conventional tissue expander comprises an expandable balloon placed beneath a patient's skin or muscle that is gradually expanded to achieve a desired expanded tissue pocket. Soft tissue expansion may have advantages over conventional skin grafting for forming the tissue pocket, including providing a natural appearance in skin texture and color by matching the surrounding skin and an existing blood supply.

Tissue expanders may be used for surgical breast reconstruction following a mastectomy. Breast reconstruction involves a multistage process in which the affected breast tissue and skin is removed in a first surgery (mastectomy). A collapsed or partially inflated tissue expander may be placed under the pectoralis major muscle behind the area of the removed breast during the first surgery to create a new breast pocket. The tissue expander may be post-operatively filled with a filler material, such as saline or air, over several days, weeks, or even months until the breast pocket achieves a desired volume to accommodate a final permanent breast implant. In a subsequent surgery, the tissue expander may be removed and replaced with the final permanent breast implant, or the breast may be reconstructed with the patient's own tissue with tissue flap surgery.

Current breast tissue expanders comprise a silicone elastomer shell with an injection port for the filler material. Breast tissue expanders typically present a round full breast shape, a partial breast shape, or a contour shape for greater lower pole volume expansion of the breast pocket. Some breast tissue expanders may further include suture tabs for suturing the tissue expander to tissue on the patient's chest wall. The suture tabs, however, are often small and difficult for the surgeon to access during surgery.

Once implanted under the pectoralis major muscle during the first-stage surgery, a fibrous capsule of scar tissue forms over the tissue expander as part of a normal physiologic response to a foreign object. This encapsulated breast pocket ultimately receives the final breast implant. The thickness of the capsule may range from thin to heavily-thickened, and the fibrous capsule formation may offer inadequate space or an undesirable shape incapable of providing a desired teardrop-shaped breast pocket. The teardrop shape of the breast pocket provides a natural-looking breast with either a round or an anatomically-shaped final permanent breast implant. The fibrous capsule may also exhibit capsular contracture, constricting the breast pocket and causing deformation of the breast pocket, excessive firmness of the breast pocket, and/or pain.

As a result, in the subsequent surgery, surgeons routinely perform an open capsulotomy to further modify the breast pocket and achieve the desired size and shape for the final permanent breast implant. The capsulotomy results in additional surgical time, complexity, and cost. Since the capsulotomy necessarily results in additional trauma to the tissue surrounding the breast pocket, the patient may experience additional pain and a longer recovery time. Further, the patient may develop complications, such as tissue necrosis, bleeding, and/or irregularities in the chest wall and/or skin.

BRIEF SUMMARY

Various embodiments provide systems and methods for a temporary extended tissue expander. Systems and methods according to various aspects of the present invention may comprise an extended tissue expander configured to increase and/or customize the size and/or shape of a breast pocket beyond the size and/or shape provided by a conventional tissue expander. The extended tissue expander may comprise a tissue expander coupled to an extension portion. In one embodiment, the extended tissue expander may preserve a breast pocket with a desired teardrop shape that does not need extensive surgical modification before placement of a final breast implant or a tissue flap.

BRIEF DESCRIPTION OF THE DRAWING FIGURES

A more complete understanding of the present invention may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. The figures described are for illustration purposes only and are not intended to limit the scope of the present disclosure in any way.

Figure 1B:
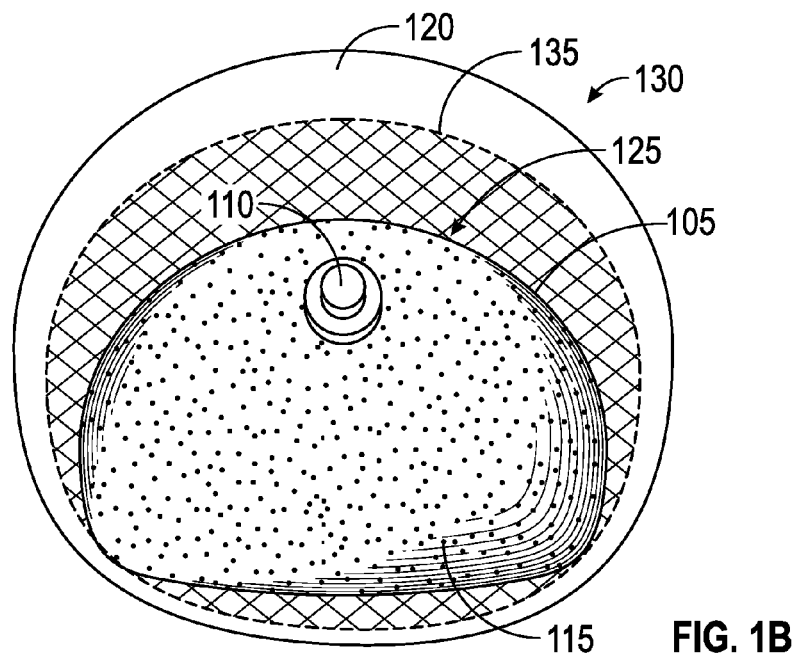
Figure 2A:
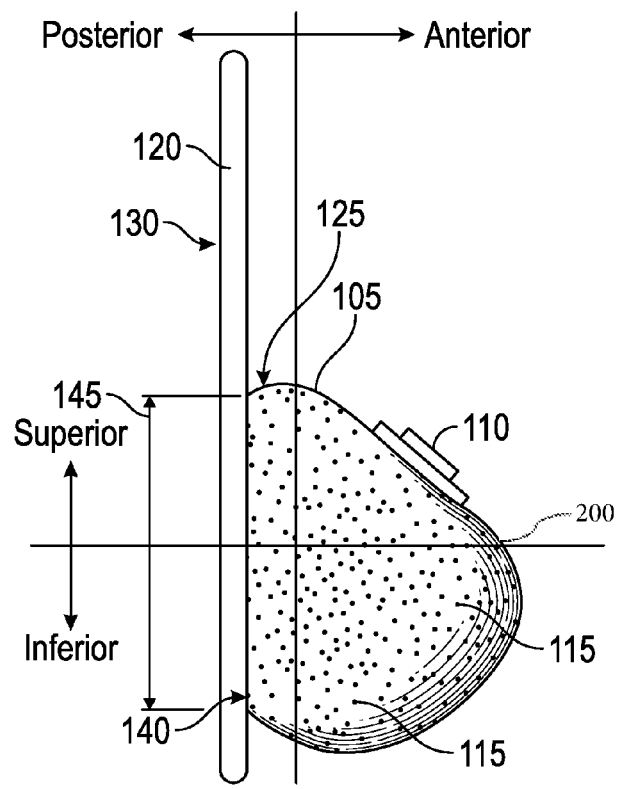
Figure 2B:
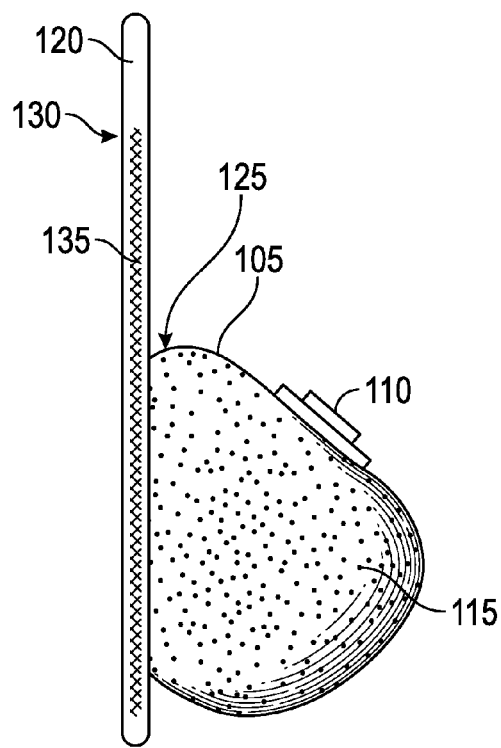
Figure 3:
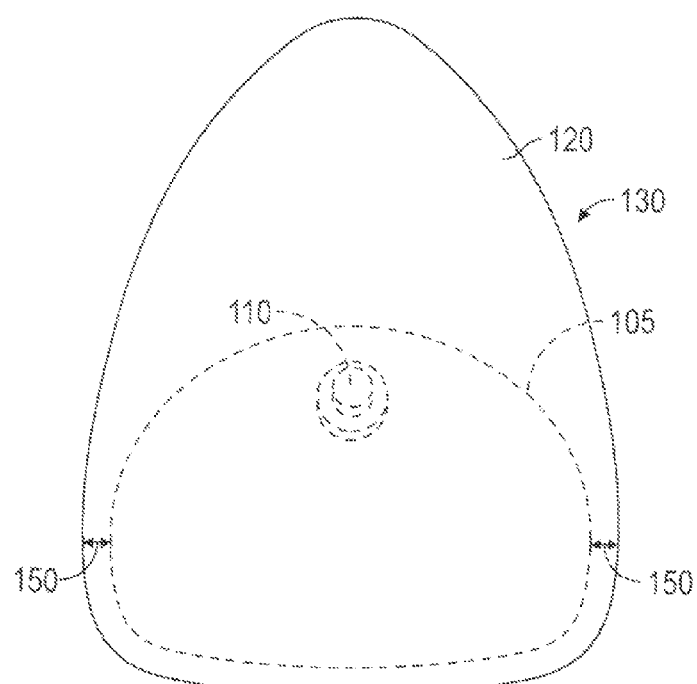
Figure 4:
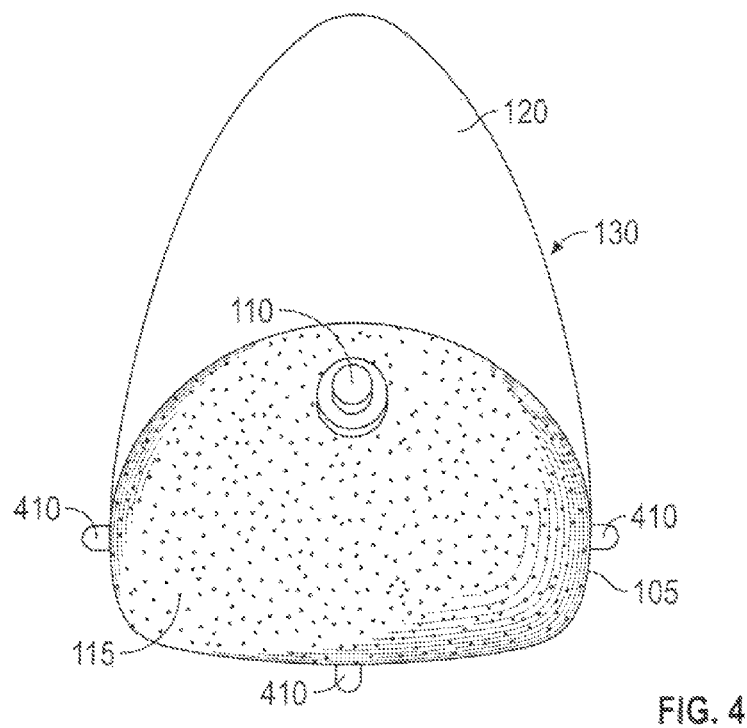
Figure 5:
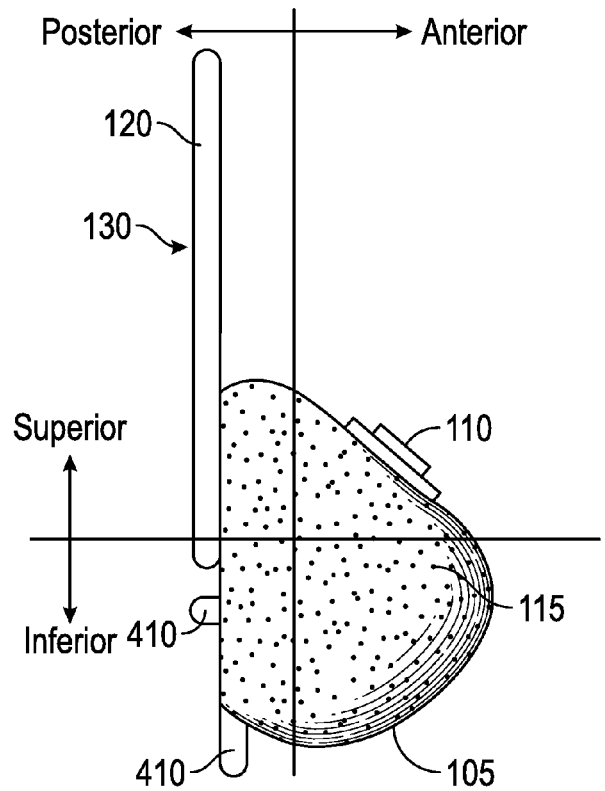
Figure 6:
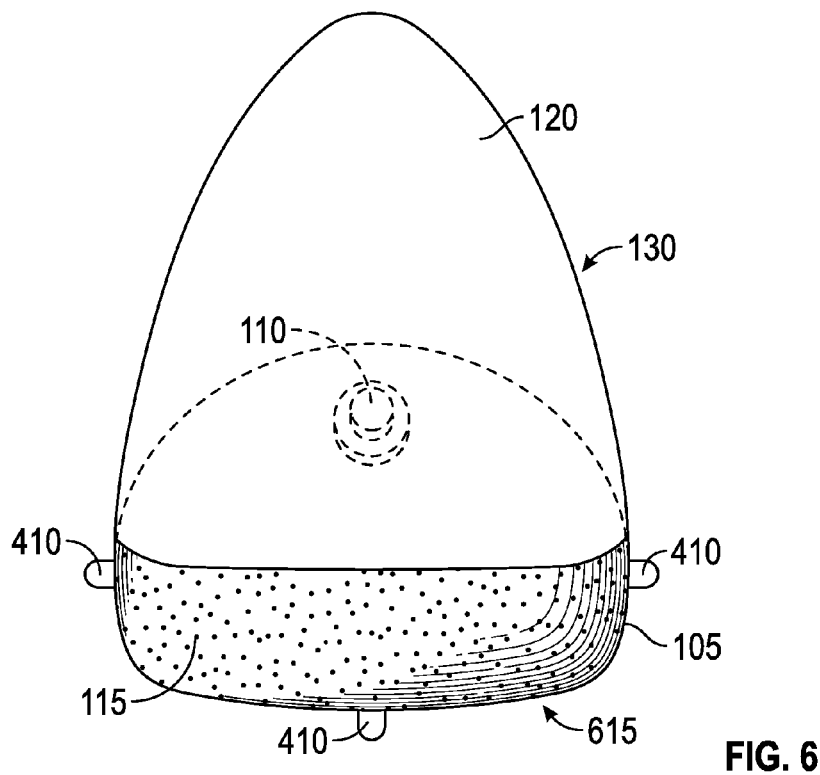
Figure 7:
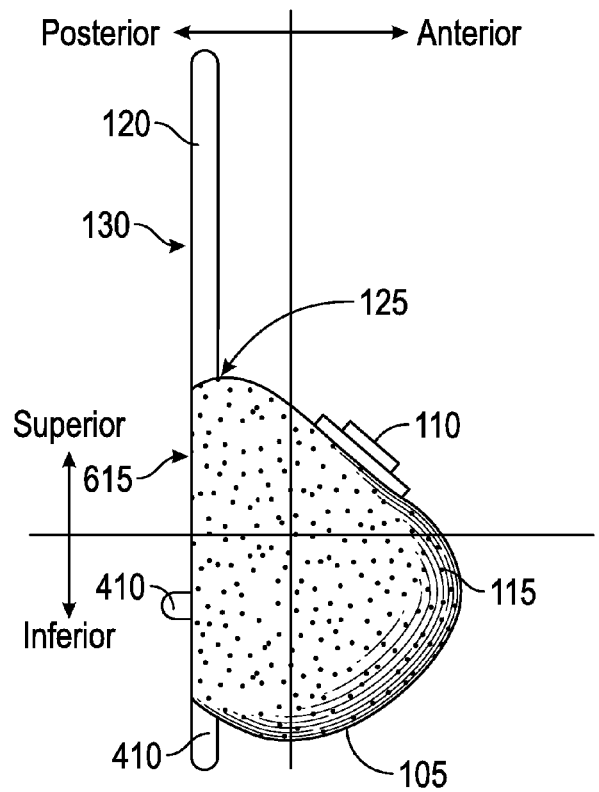
Figure 8:
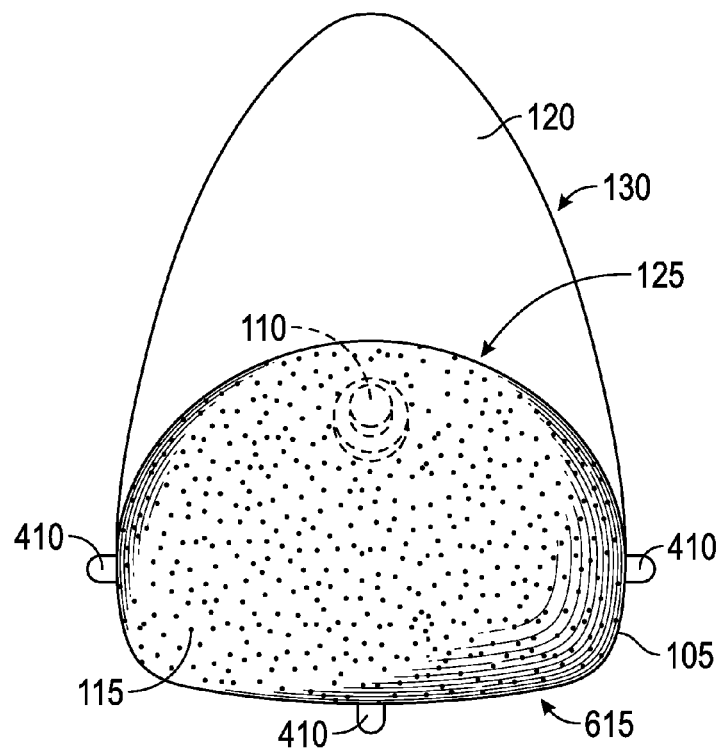
Figure 9:
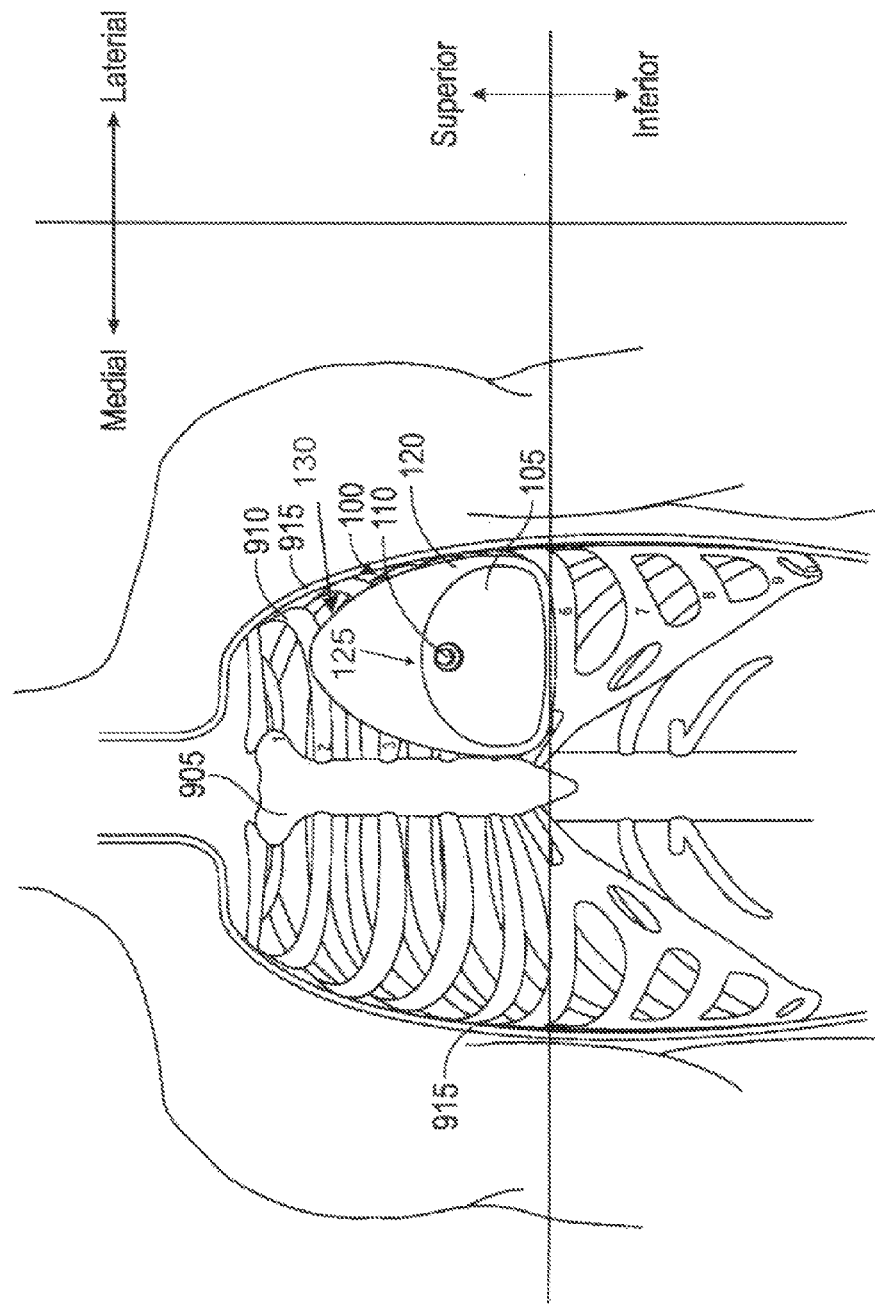
Figure 11A:
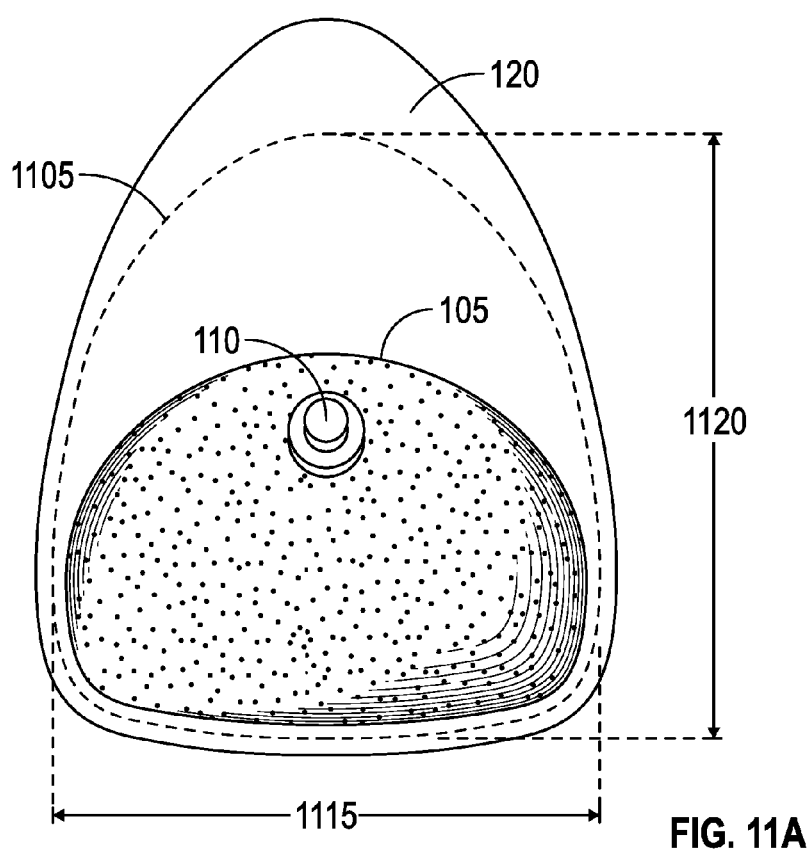
Figure 11B:
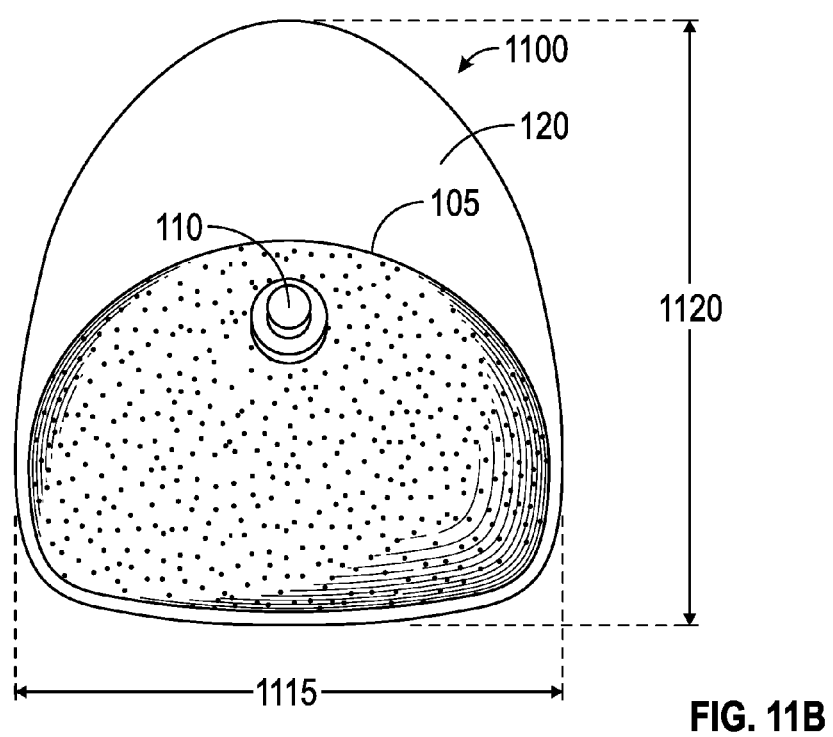
Figure 11C:
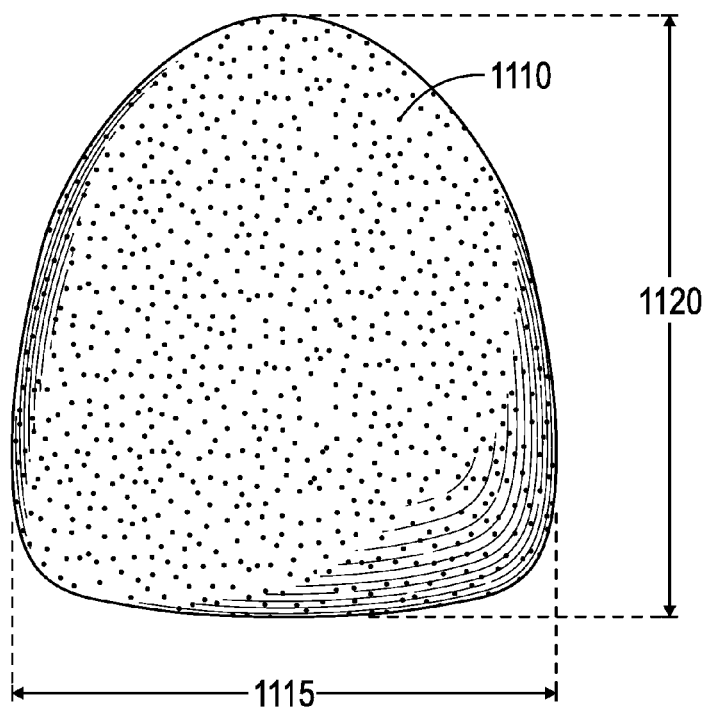
Figure 12A:
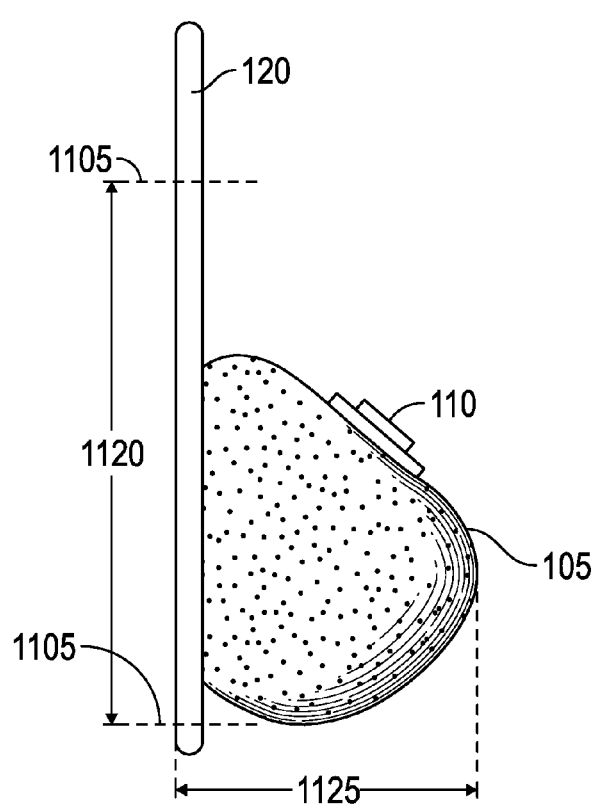
Figure 12B:
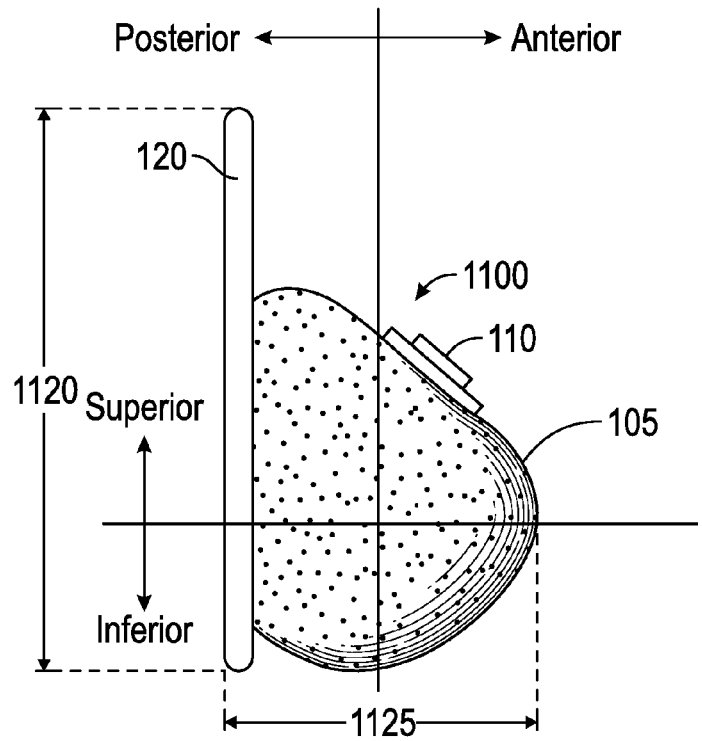
Figure 12C:
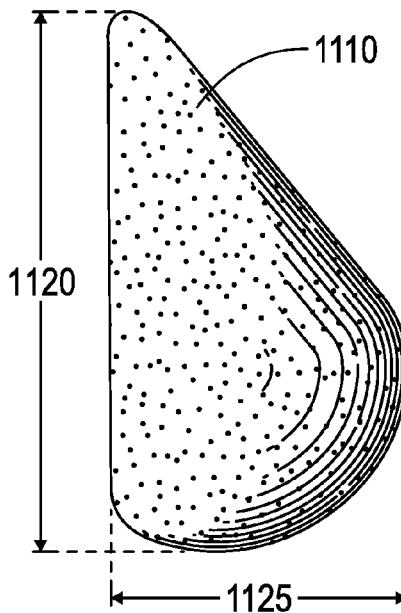
Figure 13:
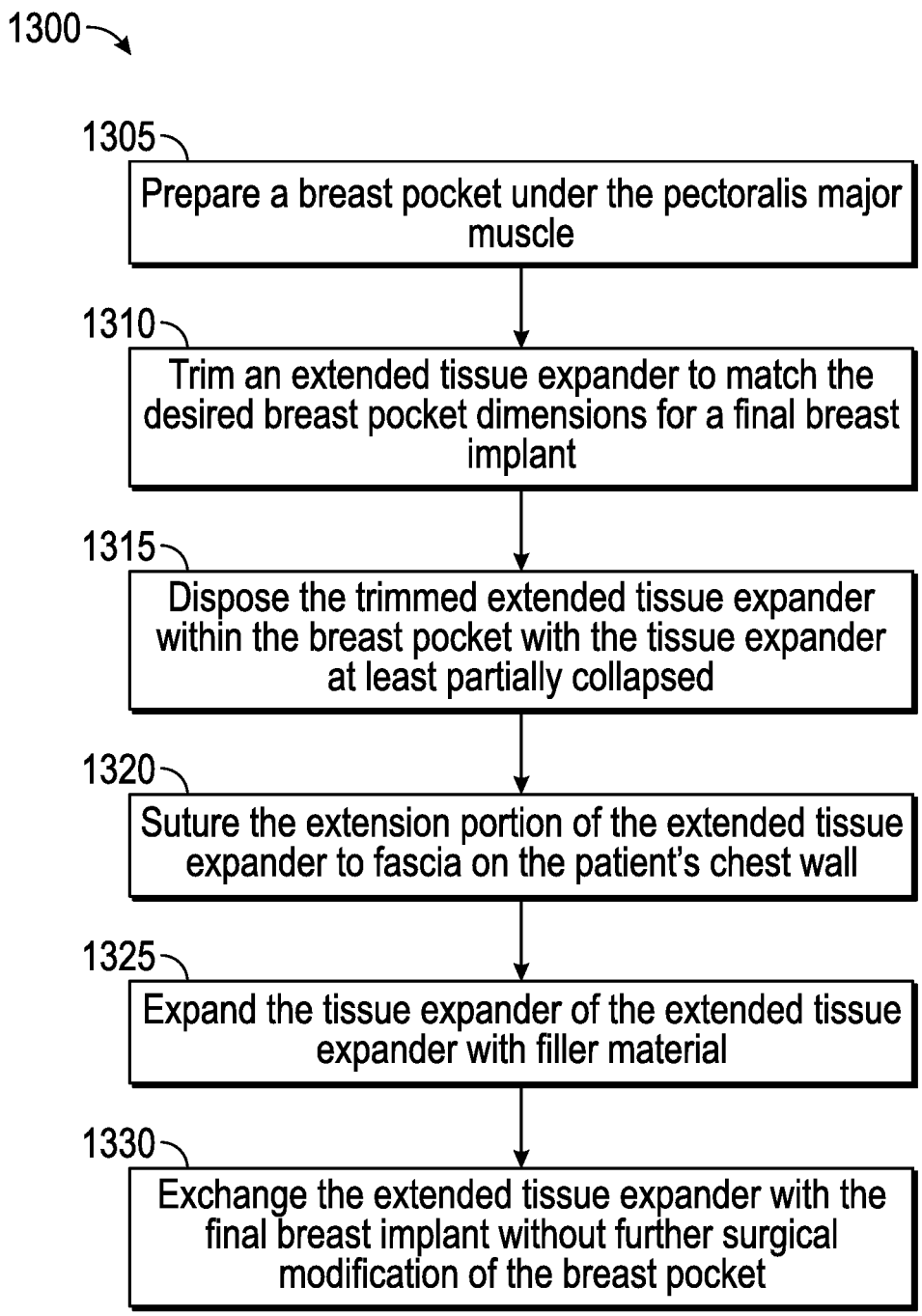
Figure 14B:
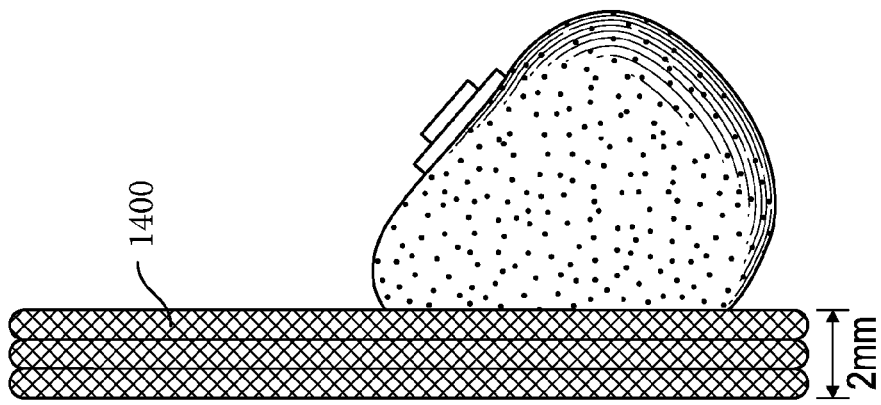
Figure 14A:
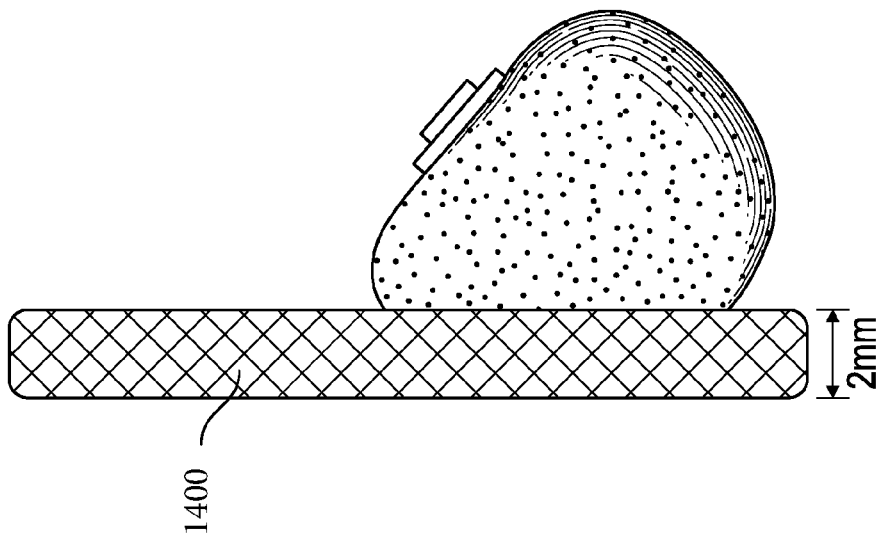
Figure 15:
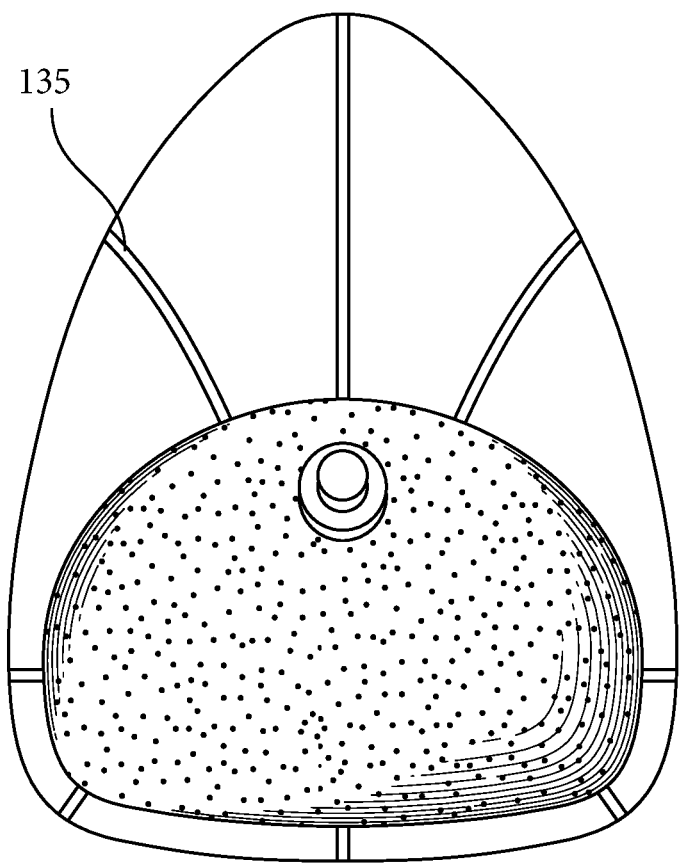
Figure 16C:
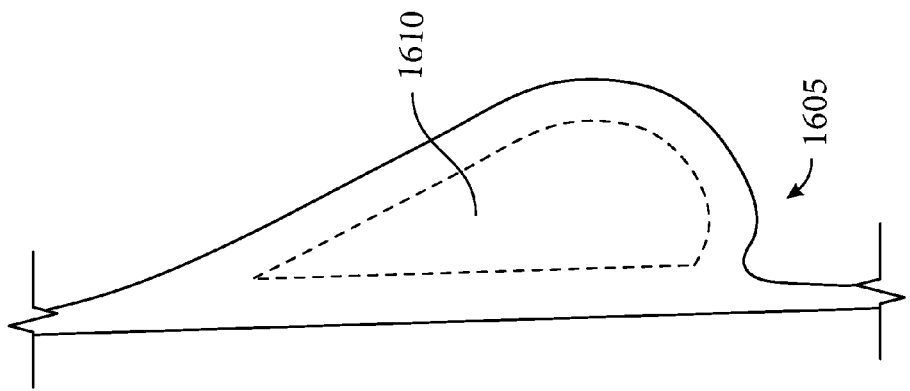
Figure 16B:
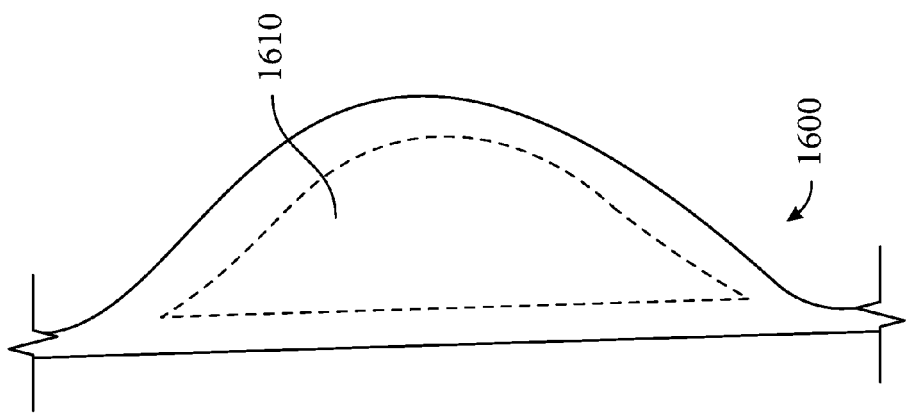
Figure 16A:
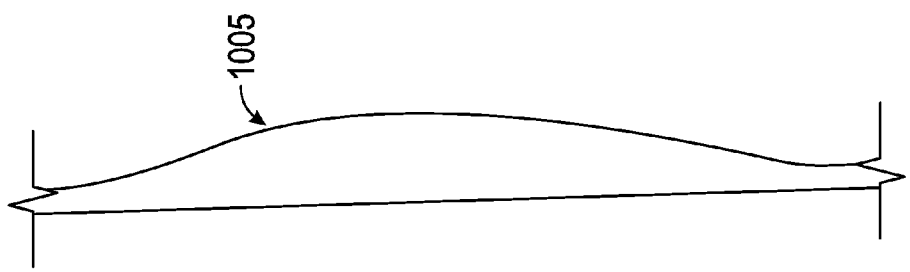
Figure 17A:
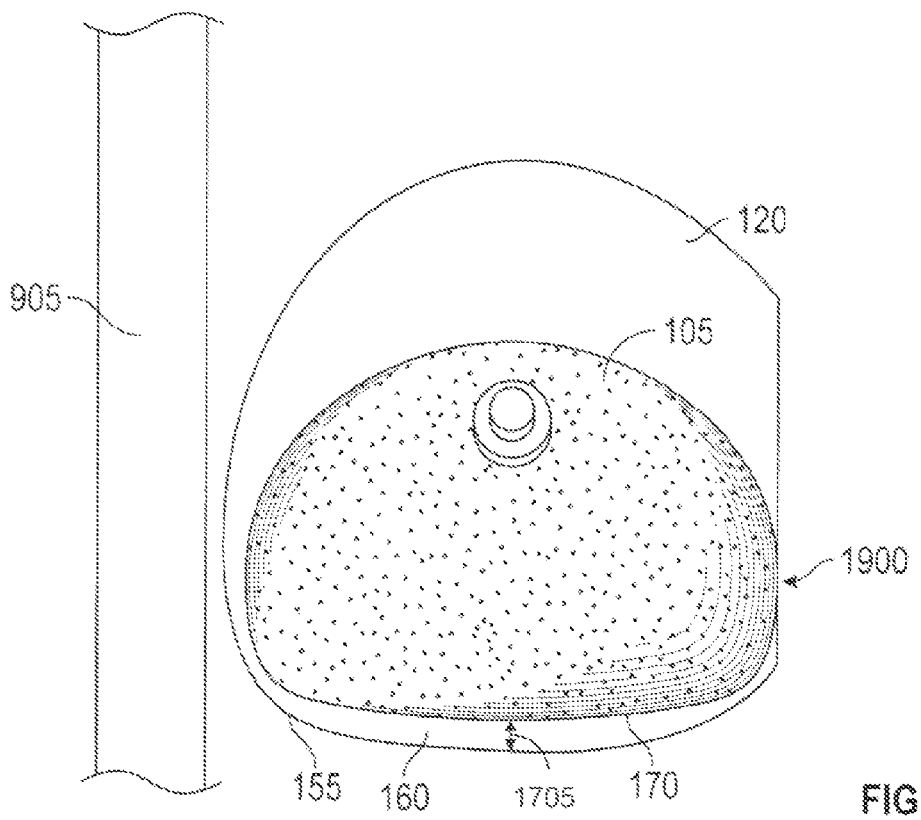
Figure 17B:
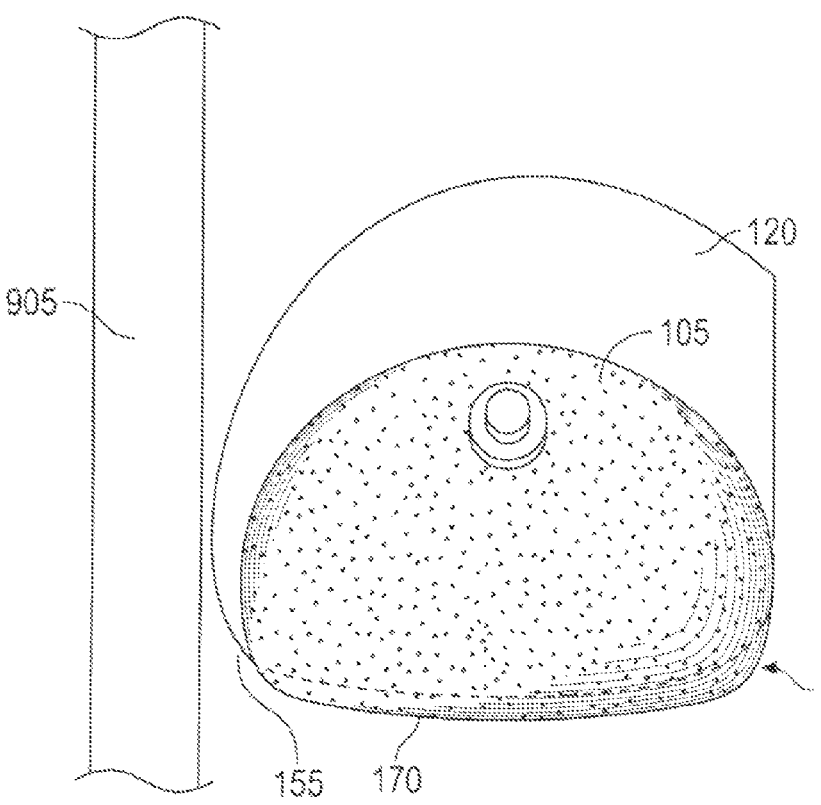

FIGS. 1A-B representatively illustrate anterior views of exemplary extended tissue expanders;

FIGS. 2A-B representatively illustrate side views of the extended tissue expanders;

FIG. 3 representatively illustrates a posterior view of an extended tissue expander;

FIG. 4 representatively illustrates an anterior view of an alternative embodiment of an extended tissue expander;

FIG. 5 representatively illustrates a side view of an alternative embodiment of an extended tissue expander;

FIG. 6 representatively illustrates a posterior view of an alternative embodiment of an extended tissue expander;

FIG. 7 representatively illustrates a side view of an alternative embodiment of an extended tissue expander;

FIG. 8 representatively illustrates a posterior view of an alternative embodiment of an extended tissue expander;

FIG. 9 representatively illustrates an exemplary extended tissue expander disposed within a breast pocket of a patient;

FIGS. 10A-C representatively illustrate side views of an extended tissue expander disposed within a breast pocket of a patient;

FIGS. 11A-C representatively illustrate the modification of an extended tissue expander along a guideline to match the dimensions of a form stable, highly cohesive silicon gel breast implant, shown with anterior views;

FIGS. 12A-C representatively illustrate the modification of the extended tissue expander along the guideline to match the dimensions of the form stable, highly cohesive silicon gel breast implant;

FIG. 13 representatively illustrates a method of using an extended tissue expander;

FIGS. 14A-B representatively illustrate side views of an extended tissue expander comprising a single-ply and a multi-ply extension portion, respectively;

FIG. 15 representatively illustrates an anterior view of an extended tissue expander with an extension portion comprising reinforcement members;

FIGS. 16A-C represent cross-section side views of desired and undesired breast shapes protruding anteriorly from a chest wall; and FIGS. 17A-C representatively illustrate anterior and side views of an extended tissue expander with a trimmed lateral edge and ptosis of the partially inflated breast tissue expander near or below the inferior border of the extension portion.

DETAILED DESCRIPTION OF EXEMPLARY EMBODIMENTS

The present invention may be described in terms of functional components and various steps. Such functional components may be realized by any number of components configured to perform the specified functions and achieve the various results. For example, methods and systems according to various aspects of the present invention may be practiced in conjunction with any number of systems and methods for tissue reconstruction, tissue expansion, and breast pocket preservation, and the systems described are merely exemplary applications for the invention. Various representative implementations of the present technology may be applied to any appropriate type of tissue expander.

The particular implementations shown and described are illustrative of the invention and its best mode and are not intended to otherwise limit the scope of the present invention in any way. For the sake of brevity, conventional manufacturing, preparation, sterilization, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

Various aspects of the invention provide methods, apparatus, and systems for making and using an extended tissue expander system, such as for reconstructive surgeries. The present detailed description of various embodiments provides a specific enabling disclosure that may be generalized to any application of the disclosed systems and methods.

Various representative implementations of the present technology may be applied to any appropriate system for tissue reconstruction. Certain representative implementations may include, for example, any suitable system or method for extending a conventional tissue expander to increase and/or customize the size and/or shape of a tissue pocket for accommodating a final implant or tissue flap. In one embodiment, the extended tissue expander system may comprise a static nonexpandable extension portion coupled to a conventional inflatable tissue expander, such as a tissue expander used for facial reconstruction or breast reconstruction following mastectomy.

In one embodiment, the combination of the static extension portion with the conventional tissue expander may maintain established soft tissue expansion methods and techniques, such as for breast tissue expansion, while providing a larger tissue pocket for accommodating the size and/or shape of the final implant and an improved surgical outcome. In one embodiment as applied to breast reconstruction, the extension portion may provide additional height to the resulting tissue pocket beyond an upper boundary of the inflated tissue expander without substantial anterior expansion away from the chest wall, resulting in a teardrop-shaped tissue pocket that may form a more natural tight shape to receive the final breast implant. The tissue expander may comprise any suitable tissue expander for expanding soft tissue, such as a breast, eyelid, and/or lip.

In an exemplary embodiment of the present invention, the extended tissue expander may be configured for submuscular breast implantation after mastectomy in a female patient to form a breast pocket comprising expanded skin. Submuscular placement of the extended tissue expander may be part of a first stage of a multi-stage breast reconstruction surgery. Submuscular placement of the extended tissue expander may also be used in the chest of a male for multi-stage male breast augmentation.

The surgeon may implant the extended tissue expander in an empty collapsed state or partially filled with a filler material. In various embodiments, the filler material comprises a conventional fluid filler material, such as a saline solution, or air. The extended tissue expander may be post-operatively filled with the filler material over time until the breast pocket reaches a desired volume. A second and/or subsequent surgery of the multi-stage surgery may occur weeks to months after the first surgery, in which the extended tissue expander may be replaced with a final breast implant or a tissue flap.

Tissue expanders and permanent implants are different devices, serve different functions, and are not interchangeable. For example, the firm, rigid structure of a tissue expander lacks the overall feel and/or consistency of a natural breast. Additionally, the extended tissue expander is inappropriate for functioning as a permanent implant because it does not have the durability required for a permanent implant. For example, the seams present within tissue expanders, such as within a fill port and a backing attached to a front expansion portion, may be held together by an adhesive that may fail, resulting in rupture substantially sooner than a permanent implant. While permanent breast implants may also leak over time, this is typically due to fatigue and failure of the silicone outer shell, as opposed to separation of the component parts of the extended tissue expander. Conversely, a permanent breast implant is typically designed to be full of filler material to maintain its breast shape and structural integrity from the moment it is manufactured.

Likewise, a permanent breast implant is not suitable as a tissue expander because the breast implant lacks the firmness and structure to allow for preferential lower pole expansion of the overlying skin and muscle. This controlled expansion is essential to produce a pocket of adequate shape and projection to create a natural looking breast with the final reconstruction. Additionally a permanent breast implant is not typically configured to expand appreciably as compared to a tissue expander and therefore cannot substantially or slowly expand skin and muscle.

Referring to FIGS. 1A-B and 2A-B, exemplary embodiments of the extended tissue expander 100 may comprise an inflatable tissue expander 105 coupled to an extension portion 120. The tissue expander 105 may comprise any suitable system or device for effecting gradual breast tissue and skin expansion or stretching. In various embodiments, the tissue expander 105 comprises a shell defining a closed interior volume to receive and retain the filler material. Referring to FIG. 2A, the shell includes an expandable anterior shell 200 that expands as the filler material is added to the interior volume. For example, the tissue expander 105 may comprise an inflatable balloon constructed from silicone elastomer or polypropylene.

The shell may further comprise a substantially nonexpandable flat posterior surface 140 that does not expand significantly as the filler material is added to the interior volume. For example, the flat posterior surface 140 may comprise different material that is substantially nonexpandable. Alternatively, the flat posterior surface 140 may comprise a thicker portion of the same material as the expandable anterior shell 200, and/or the flat posterior surface 140 may be attached to a substantially nonexpandable material to inhibit expansion.

In some embodiments, the tissue expander 105 may further comprise a port 110, such as a septum or other self-sealing integral injection port that may be pierced with a hypodermic needle, to introduce the filler material into a lumen of the tissue expander 105 for inflation. In other embodiments, the port 110 may be located remotely from the tissue expander 105. For example, the port 110 may be coupled to the tissue expander 105 through tubing (not shown) to allow the filler material to flow from the injection port 110 into the lumen of the tissue expander 105.

In some embodiments, the tissue expander 105 may be a contour profile tissue expander for extending a lower portion of the breast pocket. For example, the contour profile tissue expander may comprise or be similar to the Mentor® Contour Profile® Tissue Expander. In another embodiment, the tissue expander 105 may comprise a shape that provides directional expansion to at least a portion of the breast pocket. For example, the directionally expanding tissue expander 105 may comprise or be similar to Dacron® reinforced smooth tissue expanders produced by Mentor®, such as smooth round, smooth rectangle, smooth crescent, or smooth elliptical tissue expanders. Further, the directionally expanding tissue expander 105 may comprise or be similar to the textured or smooth crescent tissue expanders from Sientra®. Further, the directionally expanding tissue expander 105 may comprise or be similar to the Sientra® ACX™ double chamber anatomical controlled breast tissue expander which may be configured for differential inflation of one or both chambers.

In some embodiments, the tissue expander 105 may be configured to create a full breast-shaped breast pocket. For example, the tissue expander 105 may comprise or be similar to any of the Mentor® CPX2™, CPX3™, or CPX™ 4 breast tissue expanders in a low, medium, or tall height. Further, the tissue expander 105 may comprise or be similar to Allergan Natrelle® 133 Tissue Expanders. Further, the tissue expander 105 may comprise or be similar to Sientra® round breast tissue expanders or Sientra® anatomical controlled breast tissue expanders in a low, moderate, or full height.

Referring to FIGS. 4-8, in some embodiments, the tissue expander 105 may comprise one or more suture tabs 410. In one embodiment, the suture tabs 410 may be coupled to the tissue expander 105 and configured to anchor the submuscular position of the tissue expander 105 by allowing the surgeon to suture the suture tabs 410 to fascia, or other native tissues, on the patient's chest wall and/or other underlying tissue to prevent migration and/or rotation of the tissue expander 105. In some embodiments, the suture tabs 410 may comprise an elastomer such as silicone elastomer (sometimes referred to as silicone rubber). In one embodiment, the suture tabs 410 may be reinforced with a suitable biocompatible nonbioabsorbable surgical fabric, such as Dacron mesh and/or nylon.

The suture tabs 410 may be securely coupled to the tissue expander 105 by any suitable method. In one embodiment, the suture tabs 410 may be coupled to the tissue expander 105 with a biocompatible adhesive, such as a silicone adhesive. In another embodiment, the suture tabs 410 may be coextruded with the tissue expander 105. In yet another embodiment, the suture tabs 410 may be incorporated into a mold for creating the tissue expander 105.

The tissue expander 105 may comprise a smooth surface, a surface texture 115, or a combination thereof. The surface texture 115 may promote adherence of the tissue expander 105 to surrounding tissue and/or to the fibrous capsule that forms post-operatively around the extended tissue expander 100. The surface texture 115 may support immobility of the tissue expander 105 within the breast pocket during expansion of the tissue expander 105. The surface texture 115 may reduce the incidence of adverse capsular contracture that may cause deformation of the tissue expander 105.

In one embodiment, the surface texture 115 of the tissue expander 105 may comprise raised microscale nodules providing a rough feel. For example, the Mentor® tissue expanders described above may comprise SILTEX® surface texturing having microscale nodules. In another embodiment, the surface texture 115 of the tissue expander 105 may comprise surface depressions. For example, the Allergan Natrelle® 133 tissue expanders described above may comprise Biocell® surface texturing having microscale depressions.

The extension portion 120 lies against the chest wall and extends beyond an edge of the tissue expander 105, providing additional height above the tissue expander 105 within the breast pocket without substantial anterior expansion away from the chest wall. As a result, in some embodiments, the fibrous capsule may form around both the extension portion 120 and the tissue expander 105. In various embodiments, the extension portion 120 may extend beyond the upper boundary 125 of the inflated tissue expander 105 and provide less anterior expansion away from the chest wall, supporting a teardrop-shaped breast pocket that may form a more natural-shaped breast pocket for receiving the final breast implant.

The extension portion 120 may be coupled to the tissue expander 105 by any suitable method. In one embodiment, the extension portion 120 may be secured in a fixed position relative to the tissue expander 105 such that the extension portion 120 cannot rotate or otherwise move in relation to the tissue expander 105. For example, in one embodiment, the extension portion 120 may be coupled directly to the tissue expander 105 with a suitable adhesive, such as a silicone adhesive. In another embodiment, the extension portion 120 may be coupled indirectly to the tissue expander 105. For example, the tissue expander 105 may comprise a selectable fastener, such as a press stud for attachment of the extension portion 120. In yet another embodiment, the extension portion 120 may be integrated with the tissue expander 105, such as via coextrusion or including the extension portion 120 as part of a mold for the tissue expander 105. In this embodiment, the extension portion 120 and the tissue expander 105 may comprise a single continuous device.

In various embodiments, the extension portion 120 may have a uniform or variable thickness. The extension portion 120 may comprise any suitable uniform or variable thickness for maintaining an open space above the tissue expander 105 in the breast pocket by inhibiting the formation of the fibrous capsule in the space occupied by the extension portion 120. For example, in one embodiment, the extension portion 120 may be about 1.5 to 2 millimeters thick. In another embodiment, the extension portion 120 may be more than 2 millimeters thick.

The extension portion 120 may comprise any suitable extension element that may be coupled to or otherwise part of or engaging the tissue expander 105, and may comprise any suitable biocompatible material. The biocompatible material may be a nonbioabsorbable material such that the extension portion 120 remains intact for the duration of the implantation of the extended tissue expander 100. In some embodiments, the extension portion 120 may comprise a substantially static nonexpandable material, such as a sheet of silicone elastomer or polypropylene. In one embodiment, the extension portion comprises a single piece of silicone. In various embodiments, the extension portion 120 may comprise a smooth surface, a textured surface, or a combination thereof. In some embodiments, the textured surface may comprise the surface texture 115 as described above for the tissue expander 105, such as SILTEX® or Biocell® surface texturing.

The extension portion 120 material may comprise a trimmable material such that the surgeon may easily trim the extension portion 120 to fit the particular patient's needs with tools ordinarily available in the pre-surgical and surgical environment. For example, the extension portion 120 may comprise a silicone elastomer or polypropylene sheet that is sufficiently thin to be trimmed using surgical scissors or a scalpel.

Further, in some embodiments, the extension portion 120 may comprise a substantially resilient material that may be bent or folded for insertion into the breast pocket and subsequently reassume its intended shape. Resiliency of the extension portion 120 may inhibit folding in the body after implantation. Folding of the extension portion 120 may cause the patient pain, result in an improperly formed breast pocket, and allow malpositioning of the final implant in the breast pocket.

The extension portion 120 may be configured for enhanced resilience. For example, referring to FIGS. 14A-B, in some embodiments, the extension portion 120 may be about 1.5-2 millimeters thick to provide adequate resiliency in the breast pocket. The 1.5-2 millimeter thick extension portion 120 may comprise one layer (FIG. 14A) or more than one layer (FIG. 14B) of the biocompatible material. Multiple layers of the biocompatible material may be bonded together with a biologically safe adhesive. For example, in one embodiment, the extension portion 120 may comprise two layers (two-ply) or more of silicone elastomer bonded together with an adhesive, such as a silicone adhesive.

In some embodiments, the extension portion 120 may include a reinforcement material 135, for example to further improve resiliency of the extension portion's 120 shape. The reinforcement material may comprise any appropriate material, for example a resilient stiffener, such as a surgical fabric like Dacron® mesh 1400 (polyethylene terephthalate). The surgical fabric or other reinforcement material may comprise any suitable biocompatible, nonbioabsorbable, non-immunogenic, and/or inert material to provide reinforcement and/or improved mechanical integrity to the silicon elastomer or other material of the extension portion 120. The surgical fabric or other reinforcement material may comprise, for example, a natural or synthetic material that is biologically compatible with soft tissue and insoluble in body fluids. For example, referring again to FIGS. 1B and 2B, a reinforcement material 135 may comprise a nonbioabsorbable polymer, such as knitted or woven Dacron® mesh (polyethylene terephthalate). In some embodiments, the reinforcement material 135 may be fabricated from polymers, such as polyethylene, polypropylene, nylon, polytetrafluorothylene, and/or polyvinylidene fluoride. The reinforcement material 135 may also or alternatively prevent ripping or damage to the extension portion 120 upon suturing the extension portion 120 to tissue on the patient's chest wall and/or as the extended tissue expander 100 moves within the breast pocket.

The reinforcement material 135 may be included in the extension portion 120 in any suitable manner, such as embedded in an inner portion or attached to the extension portion 120. For example, in one embodiment, the reinforcement material 135 may be attached to an exterior surface of the extension portion 120, such as with a silicone-based adhesive. In another embodiment, the extension portion 120 may be coextruded with the reinforcement material 135. In yet another embodiment, the extension portion 120 may be molded around the reinforcement material 135. In yet another embodiment, the reinforcement material 135 may be embedded in the extension portion 120, for example using a sandwich construction method in which a surgical fabric is disposed between films of silicone elastomer of the extension portion 120.

For example, the reinforcement material 135 may be embedded in the silicone elastomer layers of a layered extension portion 120. In some embodiments, the reinforcement material 135 may be inserted between the layers of silicone elastomer and embedded in the silicone adhesive (FIG. 14B). In another embodiment, referring to FIG. 15, the reinforcement material 135 may be embedded into or superimposed upon the extension portion 120. For example, the extension portion 120 may comprise the reinforcement material 135 arranged in a radial pattern from a focal point in a lower pole of the extension portion and spreading outwardly toward the extension portion's outer edge.

Referring again to FIGS. 1B and 2B, the reinforcement material 135 of various embodiments may occupy a substantially central portion of the extension portion 120. For example, in some embodiments, the reinforcement material 135 or other reinforcement material may not extend to the edges of the extension portion 120 to accommodate a need to trim the extension portion 120 to a desired size and/or shape without exposing the raw edges of the reinforcement material 135 upon trimming. As a result, the edges of the reinforcement material 135 or other reinforcement material may remain sealed within the extension portion 120 after trimming and may still maintain its reinforcement capability for suturing.

In one embodiment, a variety of extended tissue expanders 100 may have different sizes of untrimmed upper portions 130, for example to accommodate the height of a petite patient or a tall patient. For example, the untrimmed upper portion 130 may be 10 centimeters for a petite patient or 15 centimeters for a tall patient. In another embodiment, the untrimmed upper portion 130 may be at least twice the height of the tissue expander 105. In yet another embodiment, the untrimmed upper portion 130 may extend just above the upper boundary 125 of the tissue expander 105 to at least three or more times the height of the tissue expander 105.

In various embodiments, at least one dimension of the extension portion 120 may be customized during the first surgery of a two-stage breast reconstruction to match the desired dimensions of the final encapsulated breast pocket that extends to a desired anatomic boundary of the patient's breast. For example, the extension portion 120 may be trimmed such that the boundaries of the breast pocket may provide a footprint of a breast with the desired dimensions on the chest wall. In some embodiments, the breast pocket having the footprint of the breast on the chest wall may provide a loose pocket needed for some types of final breast implants, such as smooth or textured round breast implants of any size that are configured to move similarly to a natural breast within the loose breast pocket.

For example, referring to FIG. 9, the upper portion 130 may be trimmed to extend the breast pocket from the upper boundary 125 of the tissue expander 105 to at least the patient's second rib to maintain an extended open pocket above the tissue expander 105. In one embodiment, the extended tissue expander 100 may be provided with an oversized untrimmed upper portion 130 of the extension portion 120 that may accommodate any patient's height. For example, the height of the upper portion 130 may be longer than the distance between the top of any patient's breast and clavicle. In one embodiment, the untrimmed upper portion 130 may be at least fifteen centimeters.

In some embodiments, the size and/or shape of the extension portion 120 may be customized prior to or during the first surgery, such as by trimming, to the precise dimensions of a preselected final breast implant, such as a form stable, highly cohesive gel breast implant of any volume. The customized extension portion 120 may provide for the formation of a tight pocket for the simple exchange of the final breast implant for the extended tissue expander 100 and obviating the need for the surgeon to perform a capsulotomy during the second surgery. Formation of the tight pocket may also prevent the need for capsulorrhaphy in a third surgery to revise the breast pocket to be smaller, resulting in reduced movement and/or altering the position of the final breast implant within the breast pocket. Capsulorrhaphy may be performed to reduce adverse unnatural looking movement or position of the final breast implant, such as lateral movement when the patient lies down, migration on the chest wall, and/or rotation of a shaped implant within the breast pocket. Capsulorrhaphy may comprise placing internal sutures along one or more borders of the breast pocket and/or the use of biomaterials, such as acellular dermal matrixes (ADMs), that provide a cell free lattice of tissue to support an ingrowth of the patient's native tissue, resulting in a smaller breast pocket.

Referring again to FIGS. 1A-B and 2A-B, in one embodiment, the extension portion 120 may be disposed along a posterior surface of the tissue expander 105 such that the length and width of the extension portion 120 exceed the length and width of the posterior surface of the tissue expander 105. Further, referring now to FIG. 9, an upper portion 130 of the extension portion 120 may be sufficiently long to extend up to at least about the patient's second rib and/or the upper portion 130 may be at least twice the height of the tissue expander 105. Referring to FIG. 3, the extension portion 120 may cover an area greater than the posterior surface of the tissue expander 105. As a result, the tissue expander 105 may not be visible from the posterior view of the extended tissue expander 100. The extension of the extension portion 120 beyond the dimensions of the posterior surface of the tissue expander 105 may provide the surgeon with ample material for suturing the extended tissue expander 100 to tissue on the patient's chest wall to prevent migration and/or rotation of the extended tissue expander 100 in the breast pocket.

Referring to FIGS. 4-6, an alternative extension portion 120 may be disposed along the posterior surface of the tissue expander 105 such that the extension portion 120 covers less than the entire posterior surface of the tissue expander 105. Referring to FIG. 6, at least a portion of a posterior surface 615 of the tissue expander 105 may be visible from the posterior view when the tissue expander 105 is coupled to the extension portion 120. Referring to FIGS. 7 and 8, another embodiment of an extension portion 120 may be disposed along the upper boundary 125 of the tissue expander 105 and extend upwards from the tissue expander 105. The entire posterior surface 615 of the tissue expander 105, or a portion of it, may be exposed.

The area of the extension portion 120 may be configured to extend to and/or cover the anatomical boundaries of the breast area in any patient. The superior boundary of the breast area in any patient is approximately at the patient's second rib. The vertical distance of the breast area in any patient is generally about twice the height 145 of the appropriately sized tissue expander 105 for each patient.

If the upper portion 130 of the extension portion 120 extends beyond the anatomical boundaries of the breast area, the resulting breast pocket created by the extended breast tissue expander may extend out of the breast area and cause multiple complications. For example, final breast shape may be deformed because the superior border of the breast pocket may be malpositioned outside the natural boundaries of the breast area. This deformation defeats a potential purpose of the extension portion 120 to form a naturally-shaped and precisely positioned breast pocket for receiving the breast implant. Additionally, the breast implant may move abnormally up toward the patients face when the patient is lying down, causing marked patient discomfort and pain.

To reach the superior boundary of the breast area at the patient's second rib, the upper portion 130 of the extension portion 120 may extend superiorly above the upper boundary 125 to a distance of about 50% of the height 145 of the tissue expander 105 when the tissue expander 105 is fully expanded for ordinary use (as opposed to the expander's tolerance limits). This vertical extension may ensure that the superior border of the resulting breast pocket is within the breast area.

In various embodiments, the extension portion 120 may not be operable at a distance of more than about 50% of the height 145 because such a distance may extend beyond the natural breast area and be too long to provide the tightly fitted teardrop-shaped breast pocket. As a result, referring to FIGS. 1A, 1B, 19A, and 19B, the extension portion 120 may be an approximately round shape such that the extension portion 120 does not appear to be particularly wider than it is long or vice versa. In some embodiments, referring to FIGS. 3, 4, 6, 8, and 9, the upper portion may be tapered. For example, the taper may be oriented such that a lower part is wider than an upper part.

Referring to FIGS. 1A-B and 2A-B, the height 145 of the tissue expander 105 may be measured according to height 145 the tissue expander's 105 flat posterior surface 140 which does not change in size upon inflation or deflation of the tissue expander 105. In some embodiments, the height 145 of the tissue expander 105 may be the distance from an inferior edge 170 to the upper boundary 125 when the tissue expander 145 is positioned in the same orientation as it is placed in the body as parallel to the patient's spine. The superior extension of the upper portion 130 of about 50% of the height 145 of the tissue expander 105 normalizes the size of the upper portion to each tissue expander's 105 size to cover only the patient's breast area. For example, a six-foot tall patient may require a tissue expander 105 having a large posterior surface 140. The associated upper portion 130 of the extension portion 120 may therefore extend superiorly according to the height 145 of this larger tissue expander as compared to a patient having a relatively petite height of five feet tall that may require a smaller tissue expander with the associated smaller upper portion 130.

In one embodiment, the extension portion 120 may extend beyond a lateral edge 165 of the tissue expander 105. Referring to FIG. 1A, an area of lateral extension may form a lateral border 155. The lateral border 155 extends out from the lateral edge 165 for a lateral distance 150. The lateral distance 150 may be a distance of less than about 10% of the height 145 of the fully expanded tissue expander 105. The lateral distance 150 of less than about 10% of the height 145 tends to ensure that the lateral edge 165 of the inflated tissue expander 105 expands past the entire lateral border 155. The lateral border 155 may be covered by the lateral edge 165 when the tissue expander 105 is inflated to ensure that the resulting breast pocket corresponds to the lateral edge 165.

A lateral distance 150 that is larger than about 10% of the height 145 may cause a breast pocket that is wider than the inflated tissue expander 105. A breast implant placed inside the breast pocket with lateral dimensions beyond the inflated tissue expander 105 may quickly become malpositioned with lateral movement toward the armpit. The breast implant may also rotate within the wide breast pocket, potentially leading to horizontal orientation of a teardrop-shaped breast implant and folding of the breast implant. The undesirable movement of the breast implant may cause an abnormal appearance of the breast and even damage to the breast implant and pain requiring further surgical procedures.

In some embodiments, one or both of the lateral extension borders 155 of the extension portion 120 may be completely removed prior to implantation by trimming away the lateral extension border 155 up to the lateral edge 165 of the tissue expander 105. In some embodiments, referring to FIGS. 17A-B, the lateral extension border 155 to be placed on the lateral portion of the chest wall farthest from the sternum 905 during surgical implantation may be removed to ensure that there are no ridges or prominence of the extension portion 120 under the skin, which may cause pain to the patient (shown as area 1900). The medially-facing edge of the extension portion placed nearest the sternum 905 during surgery may be less than 10% of the diameter of the fully expanded tissue expander 105 to inhibit encroachment on the sternum 905, which may cause medialization of both breast pockets and abnormal communication of the breast pockets across the sternum and potential movement of the breast implants across the sternum.

Referring to FIG. 17A, the inferior extension border 160 of the extension portion 120 may extend beyond the inferior edge 170 of a deflated tissue expander 105. Referring to FIG. 17B, the inferior edge 170 of an inflated tissue expander 105 may drop below and conceal the inferior extension border 160. Referring to FIG. 17C, the inferior edge 170 may correspond to the lower pole of the inflated tissue expander 105. The inferior extension border 160 may extend a distance 1705 that is sufficiently small that the inferior edge 170 of the inflated tissue expander 105 becomes the lowest point in the resulting breast pocket.

The inferior edge 170 of the inflated tissue expander 105 may cover and/or drop lower than the inferior extension border 160 to form a suitable breast pocket for the final implant. If the distance 1705 extends farther than the inferior edge 170 of the inflated tissue expander 105, then the lower boundary of the resulting breast pocket may be lower than the inflated tissue expander 105. This may lead to malpositioning of the final breast implant and/or lack of natural-looking breast ptosis.

For example, referring to FIGS. 16A-C, the breast area shape after mastectomy may be relatively flat (FIG. 16A). After tissue in the breast area is stretched with an extended tissue expander 100 having an inferior extension border 160 that extends lower on the patient than the inferior edge 170 of the tissue expander 105, the breast may fail to have the natural shape of a sloping upper portion and full hemispherical lower portion 1600 (FIG. 16B). In contrast, after breast tissue is stretched with an extended tissue expander 100 wherein the tissue expander 105 forms the lowest point of the breast pocket, the breast implant 1610 may settle into the lower pole of the breast area with natural ptosis 1605 which tends to provide natural-looking contour, mobility, and definition to the breast (FIG. 16C).

The extension portion 120 may be configured to be fixed in position within the patient, such as by suturing to the tissue of the patient's chest wall. The extension portion 120, particularly the upper portion 130, may provide the surgeon with ample material for suturing the extended tissue expander 100 to tissue on the patient's chest wall to inhibit migration and/or rotation of the extended tissue expander 100 in the breast pocket. In some embodiments, however, the extension portion 120 may not exceed the width of the tissue expander 105 and/or may not extend below the posterior surface 615 of the tissue expander 105. As a result, the extension portion 120 may not provide sufficient lateral and/or inferior material for effectively suturing the extended tissue expander 100 to the tissue.

The extended tissue expander 100 may further include suture tabs to facilitate anchoring the extended tissue expander 100 in position. For example, referring to FIGS. 4-8, suture tabs 410 may be provided on the sides and/or bottom of the tissue expander 105. The suture tabs 410 may provide anchor points for suturing the extended tissue expander 100 to the patient's fascia and/or other native tissues. For example, referring to FIGS. 7-8, the extension portion 120 may only extend from approximately the upper boundary 125 of the tissue expander 105. Therefore, the extension portion 120 may not provide lateral and/or inferior material for suturing the extended tissue expander 100 to the tissue. In one embodiment, the suture tabs 410 may be provided on the sides and/or bottom of the tissue expander 105 for additional anchor points for suturing the extended tissue expander 100 to the tissue.

Referring to FIGS. 10 and 13, an exemplary method of utilizing an extended tissue expander 100 may include preserving an upper margin 1020 of the breast pocket 1000 in the first surgery of a two-stage breast reconstruction (1300). For example, an exemplary method of using the extended tissue expander 100, according to various aspects of the present invention, may comprise surgically preparing a breast pocket 1000, such as under the pectoralis major muscle 1010 or other suitable anatomic soft tissue plane, in the breast area 1005 for implantation of the extended tissue expander 100 in the first surgery (1305).

The extended tissue expander 100 may be adapted to develop and/or maintain a desired size and/or shape of the breast pocket 1000. For example, the surgeon may customize the size and/or shape of the breast pocket by trimming the extension portion 120 according to an individual patient's anatomy and/or the size of any final breast implant. In one embodiment, the extension portion 120 may be trimmed to the desired boundaries of the final encapsulated breast pocket (1310). For example, the desired boundaries of the final encapsulated breast pocket may be considered to be a footprint of the breast or the desired breast on the chest wall. By customizing the size of the extension portion 120, a substantially simple exchange of the final breast implant for the implanted extended tissue expander 100 may be facilitated, such as during the second stage surgery of breast reconstruction.

For example, referring again to FIG. 9, the outer borders of the extension portion 120 may be trimmed to reach a patient's sternal border 905 medially, lateral chest wall 915 laterally, and second rib 910 superiorly. The inferior border of the extension portion may vary between individual patients according to their natural or desired breast position.

The extension portion 120 of the extended tissue expander 100 may be trimmed to create a breast pocket that may accommodate a pre-selected final breast implant, such as a silicone elastomer or polypropylene breast implant. In one embodiment, the outer borders of the extended tissue expander 100 may be trimmed to substantially match the desired boundaries of the final encapsulated breast pocket for use with a smooth or textured round final breast implant. In various embodiments, the extension portion 120 may be trimmed to substantially exact dimensions of a final breast implant that may require a precisely formed tight breast pocket to maintain the orientation of the final breast implant.

In one embodiment, the final breast implant may be a form stable, highly cohesive gel breast implant. The form stable, highly cohesive gel breast implant may be filled with a highly cohesive gel that retains the gel within the implant despite an implant rupture. The form stable, highly cohesive gel breast implant provides a tapered anatomical teardrop shape, unlike conventional round breast implants. Current examples of form stable, highly cohesive gel breast implants include a Mentor® MemoryShape™ Breast Implant, Allergan Natrelle® Style 410 Breast Implant, and Sientra® Silimed® Breast Implants.

The form stable, highly cohesive gel breast implant may retain its tapered shape regardless of whether it moves or rotates within the breast pocket. As a result, the breast pocket created in the first surgery of a two-stage breast reconstruction may also provide a teardrop shape that precisely matches the dimensions of the form stable, highly cohesive gel breast implant. If the breast pocket is round or too loose, the form stable, highly cohesive gel breast implant may not maintain a proper position within the breast pocket and the failure to achieve the proper breast shape may be noticeable.

The outer borders of the extended tissue expander 100 may be trimmed, such as along a guideline, to substantially match the desired breast pocket dimensions for the final breast implant, such as wherein the final breast implant is a form stable, highly cohesive gel breast implant. In one embodiment, referring to FIGS. 11A-C and 12A-C, the surgeon may cut the extension portion 120 along guideline 1105 which matches the height 1120 and width 1115 of the form stable, highly cohesive gel breast implant 1110. The resulting trimmed extension portion 1100 may be cut down to the height 1120 and width 1115 of the highly cohesive gel breast implant 1110. The trimmed extension portion 1100 may result in the extended tissue expander 100 having the substantially precise dimensions of the height 1120, width 1115, and the depth 1125 of the form stable, highly cohesive gel breast implant 1110.

In various embodiments, the guideline 1105 may comprise a virtual line, an imprinted line, a crease, and/or a perforation. In one embodiment, the surgeon may simply measure the dimensions of the final implant and trim the extension portion 120 accordingly along a virtual guideline 1105. In another embodiment, the guideline 1105 may comprise an imprinted line embedded in the extension portion 120 that may correspond to the dimensions of one or more preselected form stable, highly cohesive gel breast implants 1110. In yet another embodiment, the guideline 1105 may comprise a crease or perforation that the surgeon can quickly and easily sever during surgery such as by hand or with surgical scissors. In yet another embodiment, the extension portion 120 may be pre-trimmed to the dimensions of a preselected final breast implant, such as the form stable, highly cohesive gel breast implant 1110, obviating the need for any trimming of the extension portion 120 by the surgeon.

The breast pocket 1000 may be formed and/or maintained in conjunction with the extended tissue expander 100. The surgeon may initially form the initial breast pocket 1000 in conjunction with conventional techniques. The surgeon or other personnel may also prepare the extended tissue expander 100, for example by selecting the appropriately sized extended tissue expander 100 and/or trimming the extension portion 1100 to suit the patient. The surgeon may also fold the extension portion 1100 to initially fit into the breast pocket 1000, and then release and/or adjust the extension portion 1100 so that the resilience of the extension portion 1100 allows the extension portion 1100 to resume its form.

In various embodiments, the extended tissue expander 100 may be disposed into the breast pocket 1000, wherein the breast pocket 1000 is located in any suitable anatomic soft tissue plane in the breast area 1005. In one embodiment, as shown in FIG. 10A-C, the extended tissue expander 100 may be implanted under the pectoralis major muscle 1010. In another embodiment, the extended tissue expander 100 may be implanted above the pectoralis major muscle 1010 in the subcutaneous plane (not shown). In yet another embodiment, the extended tissue expander 100 may be implanted under other muscles in the chest wall 1015, such as the pectoralis minor, serratus anterior, or the latissimus dorsi (not shown).

For example, the extended tissue expander 100 with the trimmed extension portion 1100 may be implanted submuscularly into the patient during the first surgery of the two-stage breast reconstruction. Referring to FIGS. 10A-C, an exemplary first surgery of a two-stage breast reconstruction surgery may be performed upon a breast area 1005, for example where cancer-affected breast tissue and skin has been removed by mastectomy (FIG. 10A). An exemplary extended tissue expander 100 may be implanted into the breast pocket 1000 created by the surgeon (FIG. 10B). In one embodiment, the tissue expander 105 may be at least partially collapsed upon implantation during the first surgery. Accordingly, the breast pocket 1000 is not yet formed to the desired volume needed for the final breast implant.

In some embodiments, the extended tissue expander 100 may be used to expand the breast pocket in preparation for the second surgery in which the patient receives a tissue flap for breast reconstruction instead of the final breast implant (not shown). In a tissue flap surgery, the patient's own skin, fat, and/or muscle from another part of their body may be removed for use in reconstructing the breast or gradually moved to the breast area without severing the flap's blood supply. In one embodiment, the tissue flap may comprise skin and tissue taken from another part of the patient's body for use in reconstruction of the breast, such as a deep inferior epigastric artery perforator (DIEP) flap, a superior gluteal artery perforator (SGAP) flap, or an inferior gluteal artery perforator (IGAP) flap. In another embodiment, the tissue flap may comprise muscle in addition to skin and tissue taken from another part of the patient's body, such as a transverse rectus abdominus muscle (TRAM) flap.

In one embodiment, the extended tissue expander 100 may be disposed within the breast pocket 1000 with the tissue expander 105 at least partially collapsed (1315). The trimmed extension portion 120 and/or suture tabs 410 may be sutured to the tissue on the patient's chest wall to secure and stabilize the position of the extended tissue expander 100 in the breast pocket 1000 (1320). In one embodiment, the tissue expander 105 may be filled with filler material during and/or after surgery to gradually expand the tissue expander 105 over time until the breast pocket 1000 reaches a desired volume to accommodate the final breast implant (1325). The extended tissue expander 100 may then be exchanged with the final breast implant without further surgical modification of the breast pocket 1000, for example in conjunction with a second surgery of the two-stage breast reconstruction (1330).

Following the first surgery, the extended tissue expander 100 may be expanded over time to develop the desired breast pocket 1000. For example, referring to FIG. 10C, the inflated tissue expander 105 may expand the breast pocket 1000 to the desired dimensions to accommodate the final breast implant. The patient may then be ready for the second surgery to exchange the extended tissue expander 100 for the final breast implant. Referring to FIGS. 10B-C, the extension portion 120 may extend an upper margin 1020 of the breast pocket 1000 (corresponding to the height of the extension portion 120, such as height 1120) without excessive anterior expansion away from the chest wall 1015. The final breast pocket 1000 may have the desired teardrop shape created by the extended tissue expander 100 (FIG. 10C).

Upon formation of the desired breast pocket, the extended tissue expander 100 may be removed from the breast pocket and exchanged for the permanent implant, such as the highly cohesive gel breast implant 1110 or other implant, during the second surgery. The breast pocket created by the trimmed extension portion 1100 may reduce or prevent the need for further modification of the breast pocket during the second surgery for the implantation of the final implant, such as the form stable, highly cohesive gel breast implant 1110, into the breast pocket.

In the foregoing description, the invention has been described with reference to specific exemplary embodiments. Various modifications and changes may be made, however, without departing from the scope of the present invention as set forth. The description and figures are to be regarded in an illustrative manner, rather than a restrictive one, and all such modifications are intended to be included within the scope of the present invention. Accordingly, the scope of the invention should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present invention and are accordingly not limited to the specific configuration recited in the specific examples.

Benefits, other advantages, and solutions to problems have been described above with regard to particular embodiments. Any benefit, advantage, solution to problems, or any element that may cause any particular benefit, advantage, or solution to occur or to become more pronounced, however, is not to be construed as a critical, required, or essential feature or component.

The terms "comprises," "comprising," or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

The present invention has been described above with reference to an exemplary embodiment. However, changes and modifications may be made to the exemplary embodiment without departing from the scope of the present invention. These and other changes or modifications are intended to be included within the scope of the present invention.

What is claimed is:

1. An extended tissue expander for filling with a filler material and implantation in the breast area of a patient, comprising:
    a breast tissue expander, comprising:
        a shell defining a closed interior volume configured to retain the filler material, wherein the shell comprises:
            an expandable anterior shell; and
            a substantially nonexpandable posterior section, wherein the posterior section comprises an integrated portion of the shell; and
        a port disposed through the shell and into the interior volume; and
    an extension portion coupled to the breast tissue expander, wherein the extension portion:
        extends beyond a medial edge and a lateral edge of the breast tissue expander to a distance of less than about 10% of the height of the fully expanded breast tissue expander; and
        extends superiorly above an upper boundary of the fully expanded breast tissue expander to:
            a distance up to about 50% of the height of the fully expanded breast tissue expander, so dimensioned to reach the superior boundary of the breast area in the patient.

2. The extended tissue expander of claim 1, wherein the extension portion extends superiorly above the upper boundary of the fully expanded breast tissue expander to a distance of about 50% of the height of the fully expanded breast tissue expander.

3. The extended tissue expander of claim 1, wherein the extension portion extends below an inferior border of the breast tissue expander when the breast tissue expander is substantially deflated.

4. The extended tissue expander of claim 3, wherein the inferior border of the breast tissue expander is below an inferior border of the extension portion when the breast tissue expander is in an at least partially inflated state.

5. The extended tissue expander of claim 1, wherein the extension portion comprises a substantially round shape.

6. The extended tissue expander of claim 1, wherein the thickness of the extension portion is tapered.

7. The extended tissue expander of claim 1, wherein the extension portion has a substantially uniform thickness.

8. The extended tissue expander of claim 1, wherein the extension portion comprises a maximum thickness of at least about 1.5 millimeters.

9. The extended tissue expander of claim 1, wherein the extension portion has a maximum thickness of about 1.5 to about 2 millimeters.

10. The extended tissue expander of claim 1, wherein the extension portion comprises a trimmable material.

11. The extended tissue expander of claim 1, wherein the extension portion comprises a resilient material.

12. The extended tissue expander of claim 1, wherein the extension portion comprises a single piece of silicone.

13. The extended tissue expander of claim 12, wherein the extension portion further comprises a reinforcement material embedded into the single piece of silicone, wherein the reinforcement material enhances a resilience of the silicone.

14. The extended tissue expander of claim 1, wherein the extension portion comprises multiple layers of silicone.

15. The extended tissue expander of claim 14, wherein the extension portion further comprises a reinforcement material at least one of (a) embedded into one or more of the multiple layers of silicone and (b) disposed between two or more adjacent layers of silicone.

16. The extended tissue expander of claim 1, wherein the extension portion further comprises a reinforcement material.

17. The extended tissue expander of claim 16, wherein the reinforcement material comprises an embedded suturable surgical fabric.

18. The extended tissue expander of claim 16, wherein the extension portion further comprises a reinforcement material arranged in a radial pattern from a focal point in a lower pole of the extension portion and spreading outwardly toward the extension portion's outer edge.

19. An extended tissue expander for receiving a fluid for forming a final encapsulated breast pocket within an anatomic boundary of a patient's breast area that is configured to receive a pre-selected final breast implant or a tissue flap, the extended tissue expander comprising:
   a breast tissue expander, comprising:
      a shell configured to retain the fluid, wherein the shell comprises:
         a substantially nonexpandable backing;
         an expandable anterior shell coupled to the backing, wherein the anterior shell is integrated with the nonexpandable backing and extends anteriorly therefrom; and
         a port disposed through the shell;
      wherein the shell expands anteriorly substantially evenly as the fluid is post-operatively added to the shell through the port; and
   an approximately round extension portion coupled to the breast tissue expander, wherein the extension portion:
      extends beyond a medial edge and a lateral edge of the breast tissue expander in a fully expanded state to a distance of less than about 10% of the height of the breast tissue expander in the fully expanded state;
      extends superiorly beyond an upper boundary of the breast tissue expander in the fully expanded state to a distance of up to about 50% of the height of the breast tissue expander in the fully expanded state, so dimensioned to reach the superior boundary of the breast area in the patient;
      has a substantially uniform thickness of about 1.5 to 2 millimeters;
      substantially resiliently resumes its round shape after bending; and
      maintains an extended open pocket superiorly to the breast tissue expander to substantially correlate the dimensions of the extended tissue expander to at least one of:
         the dimensions of the final encapsulated breast pocket that extends to the anatomic boundary of the patient's breast area; and
         the dimensions of the pre-selected final breast implant to provide a tight breast pocket for the pre-selected final breast implant.

20. The extended tissue expander of claim 19, wherein the pre-selected final breast implant is a form stable, highly-cohesive silicone gel breast implant.

21. The extended tissue expander of claim 19, wherein the extension portion comprises a single piece of silicone.

22. The extended tissue expander of claim 21, wherein a reinforcement material is embedded into the single piece of silicone for shape retention.

23. The extended tissue expander of claim 19, wherein the extension portion comprises multiple layers of silicone that are coupled together.

24. The extended tissue expander of claim 23, wherein a reinforcement material is at least one of (a) embedded into one or more of the multiple layers of silicone and (b) disposed between two or more adjacent layers of silicone.

25. The extended tissue expander of claim 19, wherein the extension portion further extends below an inferior border of the breast tissue expander when the breast tissue expander is in a deflated state.

26. The extended tissue expander of claim 25, wherein the inferior border of the breast tissue expander is below an inferior border of the extension portion when the breast tissue expander is in an at least partially inflated state.

27. The extended tissue expander of claim 19, wherein the extension portion further comprises a reinforcement material arranged in a radial pattern from a focal point in a lower pole of the extension portion and spreading outwardly toward the extension portion's outer edge.

28. A method for forming a final encapsulated breast pocket within an anatomic boundary of a patient's breast area that is configured to receive a pre-selected final breast implant or a tissue flap, comprising:
   forming an initial breast pocket in the patient's breast area; and
   inserting an extended tissue expander into the initial breast pocket,
   wherein the extended tissue expander includes:
      a breast tissue expander, comprising:
         a shell defining a closed interior volume configured to retain a filler material, wherein the shell comprises:
            an expandable anterior shell; and
            a substantially nonexpandable posterior section, wherein the anterior shell is integrated with the posterior section and extends anteriorly therefrom; and
         a port disposed through the shell and into the interior volume; and
      an extension portion coupled to the breast tissue expander, wherein the extension portion:
         extends beyond a medial edge and a lateral edge of the breast tissue expander to a distance of less than about 10% of the height of the fully expanded breast tissue expander; and
         extends superiorly above an upper boundary of the fully expanded breast tissue expander to a distance up to about 50% of the height of the fully expanded breast tissue expander, wherein the distance of superior extension of the extension portion above the upper boundary of the fully expanded breast tissue expander corresponds to the superior boundary of the breast area in the patient.

29. The method for forming a final encapsulated breast pocket of claim 28, further comprising trimming the extension portion to fit a desired final encapsulated breast pocket.

30. The method for forming a final encapsulated breast pocket of claim 28, further comprising suturing the extension portion to the patient.

* * * * *